United States Patent [19]

Baude et al.

[11] 4,101,669

[45] Jul. 18, 1978

[54] STABILIZED FORMULATIONS OF 2-ALKOXYIMINO-N-CARBAMOYL-2-CYANOACETAMIDES

[75] Inventors: Frederic John Baude; Willis Eli Cupery, both of Wilmington, Del.

[73] Assignee: E. I. Du Pont de Nemours and Company, Wilmington, Del.

[21] Appl. No.: 827,595

[22] Filed: Aug. 25, 1977

Related U.S. Application Data

[60] Division of Ser. No. 639,581, Dec. 12, 1975, Pat. No. 4,053,612, which is a continuation-in-part of Ser. No. 545,605, Jan. 30, 1975, abandoned.

[51] Int. Cl.² .................. A01N 9/02; A01N 9/12; A01N 9/20

[52] U.S. Cl. .................. 424/286; 424/145; 424/304

[58] Field of Search .................. 424/304, 286, 145

[56] References Cited

U.S. PATENT DOCUMENTS

| | | | |
|---|---|---|---|
| 3,085,042 | 4/1963 | Luginbuhl | 424/286 |
| 3,379,610 | 4/1968 | Lyon et al. | 424/286 |

FOREIGN PATENT DOCUMENTS 2,312,956  9/1973  Fed. Rep. of Germany.

*Primary Examiner*—Allen J. Robinson

[57] ABSTRACT

2-Alkoxyimino-N-carbamoyl-2-cyanoacetamides are unstable in the presence of bases, even bases which are quite weak. Fungicidal compositions of these compounds are stabilized by the addition of an acidulant.

3 Claims, No Drawings

STABILIZED FORMULATIONS OF 2-ALKOXYIMINO-N-CARBAMOYL-2-CYANOACETAMIDES

This application is a division of our copending application Ser. No. 639,581, filed Dec. 12, 1975 (now U.S. Pat. 4,053,612), which is a continuation-in-part of our copending application Ser. No. 545,605, filed Jan. 30, 1975 (now abandoned).

BACKGROUND OF THE INVENTION

2-Alkoxyimino-N-carbamoyl-2-cyanoacetamides were disclosed in German Offenlegungsschrift P 2312956.8 published September 20, 1973. These compounds are agricultural fungicides particularly suited for control of late blight in tomatoes and potatoes and downy mildew in grapes.

It has been found that 2-alkoxyimino-N-carbamoyl-2-cyanoacetamides require a controlled and acidic pH for optimum chemical stability in dilute spray slurries. Surprisingly, even essentially neutral or mildly alkaline waters give significant losses of these fungicides if the spray solutions are held several hours before spraying and particularly if the spray slurry is warm. It is often desirable to mix the cyanoacetamides with other fungicides, and many commercial fungicide formulations cause significant losses of the cyanoacetamides. The problem is particularly severe with these compounds because they are normally used at very low levels (on the order of 150 ppm) while most companion fungicides are used at rates on the order of 1000 ppm or more. It is remarkable that this instability is noted only in solution. Dry powder formulations, with their normal low levels of moisture are very stable.

This invention provides formulations of 2-alkoxyimino-N-carbamoyl-2-cyanoacetamides which are stable in alkaline spray waters by combining an acidulant with the fungicidal compounds.

SUMMARY OF THE INVENTION

2-Alkoxyimino-N-carbamoyl-2-cyanoacetamides are protected from decomposition by alkaline water, adjuvants or other fungicides for example in spray slurries by formulating the cyanoacetamides with an acidulant. The 2-alkoxyiminoacetamides have the formula:

wherein
R is methyl or ethyl and
$R_1$ is hydrogen, alkyl of 1 to 4 carbon atoms or allyl.

The acidulants useful in the formulations of this invention have a pH of 2 to 5.7 when in a 1% distilled water mixture and have a free acidity of at least 2.5 millimoles per gram when titrated in such 1% aqueous mixture to a pH of 7. The ratio of the substituted iminocyanoacetamide to acidulant in the formulation of this case is from 10:1 to 10:100.

DESCRIPTION OF THE PREFERRED EMBODIMENTS

When the fungicidal alkoxyimino-N-carbamoyl-2-cyanoacetamides described above are applied as a spray slurry or solution, the pH of the solution should be maintained below 7.3 and preferably below 6.7. At a pH of 6.7, less than 10% of the cyanoacetamide decomposes in a period of 4 hours even if the solution should be warmed to 25° C to 30° C. An acidulant can be mixed in the spray slurry or solution to adjust the pH lower than 7.3, preferably lower than 6.7, but above 3.

Another method of controlling spray slurry or solution pH is to include an acidulant in the formulation of the cyanoacetamide. This is advantageous because of convenience for the applicator and, further, it insures that the product will be properly used. The acidulant should be a compound which will provide a pH in the range of 2 to 5.7 at the 1% level in distilled water and provides at least 2.5 millimoles of reserve acidity per gram when a 1% mixture in distilled water is titrated to pH 7 with sodium bicarbonate.

As a practical matter, the acidulant need not have a reserve acidity greater than about 22 millimoles per gram when titrated to a pH of 7.

The optimum quantity of acidulant will vary with the degree of stability desired and the spray mixture contemplated. In general, formulations containing from 1 to 100 parts of acidulant per 10 parts of a cyanoacetamide are useful.

Of the fungicides, preferred are:
2-cyano-N-ethylcarbamoyl-2-methoxyiminoacetamide
2-cyano-2-methoxyimino-N-methylcarbamoylacetamide
2-cyano-2-ethoxyimino-N-ethylcarbamoylacetamide
N-allylcarbamoyl-2-cyano-2-methoxyiminoacetamide
2-cyano-2-methoxyimino-N-propylcarbamoylacetamide and
N-carbamoyl-2-cyano-2-methoxyiminoacetamide.

Particularly preferred is 2-cyano-N-ethylcarbamoyl-2-methoxyiminoacetamide.

Dry solid formulations are preferred, and for this reason dry solid acidulants are preferred, although liquids can be absorbed in highly absorptive carriers and used. The acidulants can be acids, organic or otherwise, partial salts of multibasic acids, or salts or other compounds such as acid anhydrides and acid chlorides which yield an acidic reaction in water and have sufficient acidity reserve with respect to bicarbonate.

Typical of liquid acids, with which absorptive diluents may be required are:
acetic acid
propionic acid
phosphoric acid*
caprylic acid
oleic acid
pelargonic acid
lactic acid*
gluconic acid*
* Note that these acids are normally supplied in commerce as concentrated aqueous solutions.

Solid organic acids, typical of those which may be used are:
abietic acid
adipic acid
ascorbic acid
azelaic acid
benzoic acid
capric acid
chloroacetic acid
chlorobenzoic acids
citric acid
crotonic acid
fumaric acid glutonic acid
glycolic acid
iminodiacetic acid
isophthalic acid
itaconic acid
lauric acid
maleic acid
malic acid
mandelic acid
myristic acid
naphthoic acid
nitrobenzoic acid
oxalic acid
hydroxy naphthoic acid
palmitic acid
phenylacetic acid
phthalic acid
salicyclic acid
sebacic acid
sorbic acid
stearic acid
succinic acid
sulfamic acid
tartaric acid
terephthalic acid
tetrahydrophthalic acid
toluene sulfonic acid Polymeric acids, such as polyacrylic or methacrylic acids and ion exchange resins in the acid form are also suitable.

Partial salts of polybasic acids, typical of those which may be used are alkali metal-, alkaline earth-, ammonium- and substituted ammonium-:
hydrogen adipates
hydrogen azaleates
dihydrogen citrates
monohydrogen citrates
hydrogen fumarates
hydrogen isophthalates
hydrogen itaconates
hydrogen maleates
hydrogen phthalates
hydrogen sebacates
hydrogen succinates
hydrogen tartrates
hydrogen terephthalates
hydrogen sulfates
dihydrogen phosphates Typical of the salts which provide an acidic reaction with water and provide reserve acidity with respect to bicarbonate are mineral acid salts of zinc, iron and aluminum. Examples of such salts are zinc chloride, nitrate and sulfate, and the sulfates of iron and aluminum.

Anhydrides of acids mentioned above may be used. Preferred for economy are maleic and phthalic anhydrides.

Combinations of the above can be used to provide advantageous acidulant systems under some conditions.

Preferred acidulants are solid dibasic and tribasic organic acids of equivalent weight between 45 and 102, mono-basic organic acids of molecular weight between 46 and 190, and mineral acid salts of zinc.

Most preferred acidulants are succinic acid, fumaric acid, maleic acid, their monosodium salts, and zinc sulfate, chloride and nitrate.

As noted above, the fungicidal 2-alkoxyimino-N-carbamoyl-2-cyanoacetamides are often used in spray slurries or solutions at low concentrations in the range of 0.35 to $1.0 \times 10^{-3}$ M. Although natural waters may contain as much as $12-14 \times 10^{-3}$ N reserve basicity (as bicarbonate), it is exceedingly rare to find more than about $7 \times 10^{-3}$ N carbonate plus bicarbonate. Compared to these levels, any commercial fungicides in the mixture contribute relatively little to the reserve alkalinity. Furthermore, one usually need not neutralize more than half of the bicarbonate to produce an acceptable pH. Thus, no more than about 10 equivalents of acidulant per mole of cyanoacetamide is usually needed. On the other hand, a low figure for bicarbonate in well waters is about $2 \times 10^{-3}$ N, and as a minimum, about 15% should be neutralized. Thus, a formulation containing less than 0.3 equivalents of acid per mole of cyanoacetamide would have relatively narrow utility, i.e. it could be used only in water of quite low basicity and in carefully chosen mixtures. Thus, it is preferred to have from 0.3 to 10.0 equivalents of acidity per mole of cyanoacetamide. A more widely useful formulation would contain from 0.7 to 10.0 equivalents of acidity per mole of cyanoacetamide. A generally useful formulation would contain from 1.0 to 5.0 equivalents of acidity per mole of cyanoacetamide.

Many of the acids form salts with the 2-alkoxyimino-N-carbamoyl-2-cyanoacetamides. Such salts have an acidic reaction and so the acid they contain is available for neutralizing alkaline water. Thus the quantities of acid to use are the same whether the acid is in the free state or reacted with the active fungicide.

When salt formation proceeds in a packaged, relatively concentrated dry powder mixture of the cyanoacetamide and acid, the process is usually accompanied by caking and reduced dispersibility. In such cases, it is preferable to preform the salt prior to final formulation. In some cases, the salt can be formed from the acid and fungicides by precipitating from solution or simply stirring the two components in a slurry or as a wet cake. A more general procedure is to grind together the acid and substituted cyanoacetamide and allow any reaction to occur prior to formulation. Elevated temperatures in the range of 40° C to 100° C speed the process so as to permit final formulation of physically stable powder after from about a day to about an hour.

With highly inert insoluble acids such as terephthalic, the salt formation, if it occurs, proceeds so slowly as to have no practical significance. In relatively dilute formulations, say 10% cyanoacetamide or less, the loss in properties is so minor that it may not be necessary to preform the salt to avoid caking.

For practical use, formulations can be prepared in conventional ways. For use alone or in tank mixtures, the cyanoacetamide and acidulant will make up the bulk of the formulation which will generally also include surfactants and/or inert diluents. Additional small amounts of additives to reduce foam, corrosion, caking, etc may also be present. For further information concerning the art of formulation, see for example:

Off. P 2312956.8, Sept. 20, 1973.

J. B. Buchanan, U.S. Patent 3,576,834, April 27, 1971, Col. 5, Line 36 through Col. 7, Line 70 and Examples 1–4, 17, 106, 123–140.

R. R. Shaffer, U.S. Patent 3,560,616, Feb. 2, 1971, Col. 3, Line 48 through Col. 7, Line 26 and Examples 3–9, 11–18.

E. Somers, "Formulation", Chapter 6 in Torgeson, "Fungicides", Vol. I, Academic Press, New York, 1967.

Since the cyanoacetamides are used at relatively low levels, it is frequently possible to simply blend a ground mixture of compound and acidulant with already prepared commercial formulations of other fungicides to produce a one-package mixture. Of course, it is also possible to start with all of the usual ingredients and process them together to produce the final formulation.

Among fungicides useful with the cyanoacetamides are:

maneb, zineb and mancozeb
metiram
ziram, ferbam and other dimethyldithiocarbamate salts
thiram
folpet
captan
captafol
dichlofluanid
dodine
2,4-dichloro-6-(o-chloroanilino)-$\alpha$-triazine
benomyl
carbendazim
thiabendazol
methylthiophanate
chlorthalonil
"fixed coppers", such as copper oxychloride,
basic copper sulfate, copper hydroxides,
copper oxides, and copper oxychloride sulfate.

Because their fungicidal activities are complementary, combinations of the cyanoacetamides and maneb or mancozeb are particularly useful. However, maneb is unstable in the presence of acids, and the cyanoacetamides are unstable in the presence of bases. Of the acidulants listed above, only zinc sulfate, chloride or nitrate are useful with the combination of a cyanoacetamide and maneb. Zinc sulfate is particularly useful in these formulations. These salts stabilize maneb against decomposition by acids and at the same time provide acidulation to stabilize the cyanoacetamides. U.S. Pat. No. 3,085,042 and 3,379,610 teach the use of zinc salts to stabilize maneb. If sufficient zinc salt is present to stabilize the maneb, other acidulants selected from those described above may be used to protect the cyanoacetamide from attack by bases. Thus, it is essential to have at least 2 mole percent zinc ion relative to maneb present in the formulation. Of course, zinc salt which is in excess of the amount required to protect the maneb is an acidulant which protects the cyanoacetamide. As a practical matter, the formulations containing maneb and a cyanoacetamide should contain from 2 to 15 mole percent or preferably 4 to 10 mole percent zinc ion relative to maneb.

The ratio of cyanoacetamide to maneb is not critical, but the total amount of acidulant to cyanoacetamide beyond the amount of zinc required to protect the maneb must be within the limits for these materials described above.

EXAMPLE 1

| | |
|---|---|
| 2-cyano-N-ethylcarbamoyl-2-methoxyimino-acetamide | 50% |
| zinc sulfate, monohydrate | 40% |
| sodium dioctylsulfosuccinate | 1% |
| sodium alkylnaphthalenesulfonate | 1% |
| methylcellulose (15 cps grade) | 1% |
| attapulgite | 7% |

The ingredients are blended and hammer milled to produce a powder passing a U.S. #50 screen (0.3 mm opening).

The stability of the active ingredient formulated as above is compared with that of the pure technical material at 300 ppm in:

(a) a basic, soda-ash softened water of initial pH 10.2 with 0.66 × $10^{-3}$ N basicity, primarily as carbonate, and (b) a strong "sodium bicarbonate" water (prepared to match a Montana well water) with pH 8.8 and 13 × $10^{-3}$ N basicity.

After 4 hours at room temperature in these severe test waters, the following pH readings and assays (as percent of original) were obtained.

| | Water a) | | Water b) | |
|---|---|---|---|---|
| | assay | pH | assay | pH |
| pure compound | 43 | 7.7 | 16 | 8.2 |
| formulation | 78 | 6.9 | 87 | 7.2 |

Other compounds of Formula I can be formulation for the fungicide of the formation above with similar results.

EXAMPLE 2

| | |
|---|---|
| a) A powder containing: | |
| 2-cyano-N-ethylcarbamoyl-2-methoxy-iminoacetamide | 50% |
| succinic acid | 49% |
| synthetic fine silica | 1% | is prepared by blending and hammer milling.

(b) 2-cyano-N-ethylcarbamoyl-2-methoxyiminoacetamide is finely ground.

The materials above are mixed with the following commercial fungicides in a ratio to provide 1 part of active compound of (a) or (b) with the indicated parts of commodity listed:

(c) 16 parts "Parzate" — 75% zineb fungicide, Du Pont
(d) 16 parts "Thylate" — 65% thiram fungicide, Du Pont
(e) 16 parts "Phaltan" — 50% folpet fungicide, Chevron
(f) 8 parts "Benlate" — 50% benomyl fungicide, Du Pont
(g) 12 parts "Kocide" 101 — 83% cupric hydroxide fungicide, Kennecott
(h) 64 parts "Viricuivre" — 50% copper oxychloride fungicide, Pepro
(i) 16 parts Captan — 50% captan fungicide, Stauffer
(j) 24 parts "Bravo" — 75% chlorthalonil fungicide, Diamond Shamrock
(k) 16 parts "Polyram" — 80% complex dithiocarbamate fungicide, Niagara The mixtures are then added to distilled water in one case and 4.7 × $10^{-3}$ N sodium bicarbonate (chosen to represent rather alkaline water) in the other case, at a rate to provide about 150 ppm of substituted acetamide. After 4 hours, the suspensions are assayed to determine the present substituted acetamide remaining. The pH during the 1–4 hour period is also recorded.

| | | 4 Hour Assay and 1-4 Hour pH Range | | | |
|---|---|---|---|---|---|
| | | Distilled Water | | $4.7 \times 10^{-3}$N Bicarbonate | |
| | | Assay* | pH | Assay* | pH |
| "Parzate" | ac | 100 | 4.6–4.7 | 93 | 6.7–6.9 |
| mixtures | bc | 82 | 7.5–7.6 | 41 | 8.2–8.1 |
| "Thylate" | ad | 96 | 4.0–4.1 | 92 | 6.7–6.8 |
| mixtures | bd | 95 | 7.0 | 49 | 8.4–8.2 |
| "Phaltan" | ae | 100 | 4.2–4.4 | 97 | 6.7–6.8 |
| mixtures | be | 94 | 7.4–7.1 | 50 | 8.2–7.8 |
| "Benlate" | af | 100 | 4.0 | 100 | 6.7 |
| mixtures | bf | 100 | 6.9 | 55 | 8.4–8.2 |
| "Kocide" | ag | 100 | 6.1 | 92 | 6.9 |
| mixtures | bg | 77 | 7.9–7.8 | 38 | 8.5–8.3 |
| "Viricuivre" | ah | 100 | 5.6–5.7 | 100 | 6.6–6.8 |
| mixtures | bh | 99 | 7.2–7.1 | ** | 8.1–8.0 |
| Captan | ai | 100 | 5.9–6.0 | 100 | 7.0–7.2 |
| mixtures | bi | 47 | 8.3–8.0 | 48 | 8.2–7.9 |
| "Bravo" | aj | 100 | 4.2–4.5 | 100 | 6.7–6.8 |
| mixtures | bj | 84 | 7.7 | 34 | 8.4–8.2 |
| "Polyram" | ak | 100 | 4.5–4.6 | 97 | 6.8 |
| mixtures | bk | 87 | 7.5 | 49 | 8.2–8.0 |

*% of the initial 2-cyano-N-ethylcarbamoyl-2-methoxyiminoacetamide remaining after 4 hrs.
**Assay method failed.

It is apparent that the acidulant improves stability of the 2-cyano-N-ethylcarbamoyl-2-methoxyiminoacetamide in those mixtures, particularly in basic water. In no case was any loss of suspension stability noted in the mixtures.

EXAMPLE 3

| 2-Cyano-2-methoxyimino-N-methyl-carbamoylacetamide | 10% |
|---|---|
| fumaric acid | 10% |
| zinc sulfate | 2.5% |
| commercial formulated 80% maneb ("Manzate", Du Pont) | 77.5% |

The mixture is blended and ground in a hammer mill.

The powder is added at the 0.15% level to $4.7 \times 10^{-3}$ N sodium bicarbonate test water and held for 4 hours. At that time, well over 90% of the substituted acetamide remains and the pH is stable at about pH 6.7. A similar formulation without the acidulant system produces a pH which ranges from 8.4 to 7.9, and only about 23% of the original substituted acetamide remains after 4 hours.

EXAMPLE 4

| 2-Cyano-2-methoxyimino-N-propyl-carbamoylacetamide | 30% |
|---|---|
| terephthalic acid | 60% |
| synthetic fine silica | 8% |
| sodium alkylnaphthalenesulfonate | 0.5% |
| methylated cellulose (15 cps grade) | 1.5% |

The ingredients are blended and passed through a hammer mill to produce a powder passing a U.S.S. #50 screen (0.3 mm openings). When held in natural alkaline water, this formulation exhibits improved stability over conventional formulations without acidulant. All solid acidulants of the invention can be substituted for terephthalic acid, in the example above, with similar results.

As noted above, with some acids of the invention, shelf life may be limited by salt formation in storage and the products may cake. When it is desired to avoid this, the formulation should be heated overnight to 50° C to 80° C and reground.

EXAMPLE 5

The biological effectiveness of the acidulated formulation of Example 1 is compared with that of an unacidulated formulation prepared as follows:

| 2-cyano-N-ethylcarbamoyl-2-methoxyiminoacetamide | 80% |
|---|---|
| sodium dioctylsulfosuccinate | 1% |
| sodium ligninsulfonate | 2% |
| Kaolinite | 17% |

The ingredients are blended and hammer milled.

Spray mixtures are prepared at 80 ppm active ingredient in distilled water and in water a) of Example 1, and are held 5 hours before spraying tomato plants. The plants are allowed to stand overnight before inoculation with late blight fungus spores. The control indicated is obtained.

| | % Control of Tomato Late Blight | |
|---|---|---|
| Formulation | Distilled water | Water a) |
| acidulated | 100 | 99 |
| unacidulated | 100 | 0 |

EXAMPLE 6

A mixture of 383 parts technical 2-cyano-N-ethylcarbamoyl-2-methoxyiminoacetamide in 2055 parts methanol is heated to form a solution, and 117 parts of commercial fumaric acid is added with continued heating. When solution is complete, the solution is cooled, and the precipitate filtered and dried to yield 428 parts of a salt comprising 2 moles of cyanoacetamide per mole of fumaric acid. The methanol can be recycled several times and yields 490–495 parts of salt in succeeding runs.

Ten parts of the salt can be combined with the following ingredients

| Fumaric acid | 2.8 parts |
|---|---|
| Sodium dioctylsulfosuccinate | 1.0 part |
| Attapulgite | 6.2 parts |
| Commercial mancozeb (Manzate ® 200) | 80.0 parts |

The ingredients are combined and passed through a hammer mill to produce a powder passing a U.S.S. #50 sieve (0.3 mm opening). The product is stable for an extended period when slurried at 1500 ppm in alkaline water of $5.5 \times 10^{-3}$ N reserve alkalinity and has good fungicidal activity.

EXAMPLE 7

A thick slurry of 383 parts of technical 2-cyano-N-ethylcarbamoyl-2-methoxyiminoacetamide and 117 parts of commercial fumaric acid in 1200 parts of water is stirred mechanically for 20 minutes, filtered and dried. This salt can be combined with other ingredients as described below to produce a physically stable wettable powder.

| Salt as described above | 25.8% |
|---|---|
| Fumaric acid | 50.2% |
| Sodium dioctylsulfosuccinate | 1.0% |
| Sodium ligninsulfonate | 3.0% |
| Attapulgite | 20.0% |

The mixture is blended and passed through a hammer mill to produce a powder. The formulation disperses readily both before and after extended storage and gives chemically stable suspensions in natural alkaline water.

EXAMPLE 8

| | |
|---|---|
| 2-Cyano-N-ethylcarbamoyl-2-methocyiminoacetamide | 20% |
| Fumaric acid | 56% |
| Sodium dioctylsulfosuccinate | 1% |
| Sodium ligninsulfonate | 3% |
| Attapulgite | 20% |

The ingredients are passed through a hammer mill to produce a powder passing 50-mesh. The powder is held overnight at 85° C and then reground through the hammer mill. A physically stable formulation with good properties results.

EXAMPLE 9

| | |
|---|---|
| Commercial copper oxychloride* | 96.29% |
| -2-Cyano-N-ethylcarbamotl-2-methoxyiminoacetamide | 2.25% |
| Fumaric acid | 1.46% |

*Pepro "Viricuivre", 50% Cu

The ingredients are combined and passed through a hammer mill to produce a wettable powder which has good fungicidal activity when used even in alkaline water. The acidulation does not cause phytotoxicity.

We claim:

1. A fungicidal composition consisting essentially of
(a) 10 parts of a compound of the formula 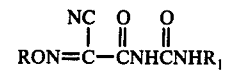 wherein
R is methyl or ethyl, and
$R_1$ is hydrogen, alkyl of 1–4 carbon atoms or allyl;
(b) a fungicidally effective amount of zineb; and
(c) from 1 to 100 parts of an acidulent having a pH of 2 to 5.7 in a 1% distilled water mixture and a free acidity of from 2.5 millimoles per gram to 22 millimoles per gram of acidulent when titrated in a 1% distilled water mixture to a pH of 7.

2. The composition of claim 1 wherein
R is methyl and
$R_1$ is ethyl.

3. A composition of claim 1 wherein R is methyl, $R_1$ is ethyl and the acidulant is selected from the group consisting of dibasic and tribasic organic acids of equivalent weight between 45 and 102, monobasic organic acids of equivalent weight between 46 and 190 and mineral acid salts of zinc.

* * * * *